United States Patent
Quaglia et al.

(10) Patent No.: US 9,635,851 B2
(45) Date of Patent: May 2, 2017

(54) WATER SOLUBLE POLYMERS FOR AGROCHEMICAL COMPOSITIONS

(71) Applicant: LAMBERTI SPA, Albizzate (VA) (IT)

(72) Inventors: Filippo Quaglia, Novate Milanese (IT); Dario Fornara, Novara (IT); Rocco Di Modugno, The Woodlands, TX (US); Cristina Picco, Oleggio (IT); Alessandro D'Aloia, Novi Ligure (IT); Arianna Benetti, Sesto Calende (IT); Giovanni Floridi, Novara (IT); Giuseppe Li Bassi, Gavirate (IT)

(73) Assignee: LAMBERTI SPA, Albizzate (VA) (IT)

( * ) Notice: Subject to any disclaimer, the term of this patent is extended or adjusted under 35 U.S.C. 154(b) by 0 days.

(21) Appl. No.: 14/893,664

(22) PCT Filed: May 21, 2014

(86) PCT No.: PCT/EP2014/060485
§ 371 (c)(1),
(2) Date: Nov. 24, 2015

(87) PCT Pub. No.: WO2014/191288
PCT Pub. Date: Dec. 4, 2014

(65) Prior Publication Data
US 2016/0106092 A1 Apr. 21, 2016

(30) Foreign Application Priority Data
May 27, 2013 (IT) ............... VA2013A0029

(51) Int. Cl.
| | | |
|---|---|---|
| A01N 25/04 | (2006.01) |
| A01N 25/30 | (2006.01) |
| A01N 37/18 | (2006.01) |
| A01N 43/36 | (2006.01) |
| A01N 43/42 | (2006.01) |
| A01N 43/653 | (2006.01) |
| A01N 43/707 | (2006.01) |
| A01N 37/34 | (2006.01) |
| A01N 43/40 | (2006.01) |
| A01N 43/50 | (2006.01) |
| A01N 43/54 | (2006.01) |
| A01N 43/58 | (2006.01) |
| C08F 22/02 | (2006.01) |
| C08F 220/28 | (2006.01) |
| C08G 81/02 | (2006.01) |

(52) U.S. Cl.
CPC ............. *A01N 25/04* (2013.01); *A01N 25/30* (2013.01); *A01N 37/18* (2013.01); *A01N 37/34* (2013.01); *A01N 43/36* (2013.01); *A01N 43/40* (2013.01); *A01N 43/42* (2013.01); *A01N 43/50* (2013.01); *A01N 43/54* (2013.01); *A01N 43/58* (2013.01); *A01N 43/653* (2013.01); *A01N 43/707* (2013.01); *C08F 22/02* (2013.01); *C08F 2220/285* (2013.01); *C08G 81/025* (2013.01)

(58) Field of Classification Search
None
See application file for complete search history.

(56) References Cited

U.S. PATENT DOCUMENTS

| | | |
|---|---|---|
| 5,139,773 A | 8/1992 | Tadros |
| 5,320,672 A | 6/1994 | Whalen-Shaw |
| 6,093,764 A | 7/2000 | Egraz et al. |
| 6,767,865 B2 | 7/2004 | Tandt et al. |
| 2006/0142159 A1 | 6/2006 | Meyer et al. |

FOREIGN PATENT DOCUMENTS

| | | |
|---|---|---|
| WO | 2008015185 A2 | 2/2008 |
| WO | 2010121976 A2 | 10/2010 |

*Primary Examiner* — Mina Haghighatian
*Assistant Examiner* — Luke Karpinski
(74) *Attorney, Agent, or Firm* — Mossman, Kumar & Tyler, PC

(57) ABSTRACT

Agrochemical aqueous compositions containing at least one organic, solid agrochemically active ingredient which is insoluble in water and, as dispersing and wetting agent, a water soluble polymer based on one or more ethylenically unsaturated carboxylic acids, from 5% to 55% of the carboxylic groups of said water soluble polymer being esterified with a polyalkoxylated polystyrylphenol.

23 Claims, No Drawings

WATER SOLUBLE POLYMERS FOR AGROCHEMICAL COMPOSITIONS

TECHNICAL FIELD

The present invention relates to agrochemical aqueous compositions containing at least one organic, solid agrochemically active ingredient which is insoluble in water and, as dispersing and wetting agent, a carboxylated water soluble polymer based on one or more ethylenically unsaturated carboxylic acids, from 5% to 55% of the carboxylic groups of said water soluble polymer being esterified with a polyalkoxylated polystyrylphenol.

BACKGROUND ART

Pesticides, depending on the characteristics of the active substance that they contain and on their use, may be formulated as dry powders, wettable powders, dispersible granules, concentrated suspensions, concentrated emulsions and solutions, and their application on the soil, seeds and plants foliage generally occurs in the form of aqueous solution, suspension or emulsion.

In case the active substance is solid and insoluble in water, in order to disperse and suspend it in water, surfactants, that can be polymeric or non-polymeric, are normally employed; beside assisting the formation of mixtures of water and water insoluble materials, the surfactants reduce the interfacial tension between water and the treated substrate and improve the distribution and penetration of the active substance. They are generally said to act as dispersants, wetting agents and penetration enhancers.

Wetting/dispersing agents that are commonly used in the preparation of agrochemical compositions containing solid active ingredients which are insoluble in water are, for instance, sodium lignosulfonates, sodium naphthalene sulfonate/formaldehyde condensates, tristyrylphenolethoxylate phosphate esters, ethylene oxide/propylene oxide block copolymers.

A variety of polyacrylic polymeric surfactants is known to act as dispersants, milling and wetting agents for agrochemical compositions; in polyacrylic polymeric surfactants, one portion of the structure is typically made hydrophilic by inserting polyethoxylated segments, carboxylic acid groups, sulfonic acid groups, while the hydrophobic portion of the structure typically contains fatty alkyl chains, aryl groups, polypropoxylated segments.

Among the polyacrylic polymeric surfactants, particularly those that are obtained by copolymerisation of monomers containing strongly acidic groups such as sulfonic groups, are known and have been appreciated since a long time.

US 2006/0142159 describes the use of polymers obtained by radical polymerisation of 2-acrylamido-2-methylpropanesulfonic acid and/or salt thereof with one or more hydrophobic macromonomers, as stabilisers for concentrated suspensions.

WO 2008/015185 discloses pesticidal agrochemical compositions, characterised by the fact that they comprise from 0.5 to 10% by weight of a polymer obtained by polymerising: a) from 60 to 90% molar of acrylic or methacrylic acid and/or 2-acrylamido-2-methylpropanesulfonic acid; b) from 10 to 40% molar of an acrylic or methacrylic acid ester of a $C_8$-$C_{18}$ alcohol.

WO 2010/121976 relates to agrochemical formulations comprising an agrochemical active and a dispersant which is a copolymer of olefinically unsaturated carboxylic acids and its salts, olefinically unsaturated monomers bearing a hydrophobic moiety and, optionally, olefinically unsaturated sulfonic acid or phosphonic acids monomers and its salts; examples are given for the use of benzylmethacrylate, acrylic acid and 2-acrylamido-2-methylpropanesulfonic acid copolymers.

More examples of polyacrylic polymeric dispersants for agrochemical compositions are given in U.S. Pat. No. 6,767,865 (styrene/(meth)acrylic acid copolymers) and in U.S. Pat. No. 5,139,773 (methyl methacrylate/methacrylic acid/methoxy (polyethyleneglycol) methacrylate copolymers).

Similar polyacrylic polymeric dispersants are also known to disperse inorganic materials in water.

U.S. Pat. No. 6,093,764 relates to polymeric dispersants based on at least one monomer which is ethylenically unsaturated and has a carboxylic function and at least one surface-active oxyalkylated monomer which is ethylenically unsaturated and terminates with a hydrophobic chain; the dispersants are prepared by radical copolymerization of the monomers. The dispersants of U.S. Pat. No. 6,093,764 are useful for dispersing in water mineral substances, such as calcium carbonates, calcium sulphate, titanium dioxide, talc, mica and other minerals.

U.S. Pat. No. 5,320,672 describes associative dispersants for pigments, particularly for dispersing kaolin clay in a paper coating composition, that are the sodium salt of acrylic acid copolymerized with an acrylate ester containing 20 moles of ethylene oxide and phenyl stearyl hydrophobes.

It has now been found that the use, as dispersing and wetting agent, of a carboxylated water soluble polymer based on one or more ethylenically unsaturated carboxylic acids, from 5% to 55% of the carboxylic groups of said water soluble polymer being esterified with a polyalkoxylated polystyrylphenol, provides unexpected advantages in the preparation of agrochemical compositions comprising at least a water insoluble solid organic pesticide.

The water soluble carboxylated polymer ("water soluble polymer") may be prepared in two steps by i) radically polymerizing the ethylenically unsaturated mono carboxylic acids, bi-carboxylic acids or anhydride thereof, and ii) esterifying in a subsequent step the thus obtained carboxylated polymer with specific amounts of the polyalkoxylated polystyrylphenol.

The water soluble carboxylated polymer according to the invention behaves as a very good dispersing agent in grinding water insoluble organic agrochemically active substances which are to be dispersed in water; furthermore, the polymer is very efficient in promoting the formation of stable concentrated aqueous systems comprising the water insoluble organic agrochemically active substances and it helps their final dilution in water.

Therefore, the aqueous agrochemical composition of the invention is advantageously a suspension concentrate (SC) in which the water insoluble organic agrochemically active substance is suspended in water at concentration from about 50 to about 1100 g/l.

Suspension concentrates are stable liquid suspensions of very small pesticide particles that offer many advantages, such as ease of handling and dosing, safety to the operator and the environment, and economy.

Because of the hydrophobicity and low density of most of the water insoluble organic agrochemically active substances, the preparation of their stable suspension concentrate is often a challenging objective and requires the accurate tailoring of the wetting and dispersing agents. Most often, combination of different substances, each performing a specific function (as milling agent, thinner, wetting agent, dispersant) are required.

It is therefore highly desirable in the field to provide a versatile unique chemical that is able to perform all the above functions in the preparation of stable suspension concentrates of different insoluble organic agrochemically active substances, even in admixture.

SUMMARY OF THE INVENTION

One object of the present invention is an agrochemical aqueous composition containing at least one solid organic agrochemically active ingredient that is insoluble in water and a carboxylated water soluble polymer in which a) at least 85% by moles of the monomer units derive from ethylenically unsaturated $C_3$-$C_5$ mono carboxylic acids, bi-carboxylic acids or anhydride thereof and from 0 to 15% by moles of the monomer units derive from one or more non-carboxylated ethylenically unsaturated monomers, b) from 5% to 55% of the carboxylic acid groups of the polymer are esterified with a at least one polyalkoxylated polystyrylphenol.

Another object of the invention is a carboxylated water soluble polymer in which a) at least 85% by moles of the monomer units derive from ethylenically unsaturated $C_3$-$C_5$ mono carboxylic acids, bi-carboxylic acids or anhydride thereof and from 0 to 15% by moles of the monomer units derive from one or more non-carboxylated ethylenically unsaturated monomers, b) from 5% to 55% of the carboxylic acid groups of the polymer are esterified with at least one polyalkoxylated polystyrylphenol, the water soluble polymer being obtained by i) radically polymerizing at least 85% by moles of ethylenically unsaturated $C_3$-$C_5$ mono carboxylic acids, bi-carboxylic acids or anhydride thereof and from 0 to 15% by moles of one or more non-carboxylated ethylenically unsaturated monomers, ii) esterifying the thus obtained carboxylated polymer with from 5% to 55% of equivalents, based on the carboxylic acid groups of the polymer, of a polyalkoxylated polystyrylphenol.

Still another object of the invention is a process for the preparation of a water soluble carboxylated polymer in which a) at least 85% by moles of the monomer units derive from ethylenically unsaturated $C_3$-$C_5$ mono carboxylic acids, bi-carboxylic acids or anhydride thereof and from 0 to 15% by moles of the monomer units derive from one or more non-carboxylated ethylenically unsaturated monomers, b) from 5% to 55% of the carboxylic acid groups of the polymer are esterified with a at least one polyalkoxylated polystyrylphenol, the water soluble polymer being obtained by i) radically polymerizing at least 85% by moles of ethylenically unsaturated $C_3$-$C_5$ mono carboxylic acids, bi-carboxylic acids or anhydride thereof and from 0 to 15% by moles of one or more non-carboxylated ethylenically unsaturated monomers, ii) esterifying the thus obtained carboxylated polymer with from 5% to 55% of equivalents, based on the carboxylic acid groups of the polymer, of a polyalkoxylated polystyrylphenol.

The characteristics and advantages of using the water soluble carboxylated polymer according to the present invention are illustrated in detail in the following description.

DETAILED DESCRIPTION

In the present application, the terms "pesticide", "agrochemically active substance", "agrochemically active ingredient" are used as synonyms and refers to the chemical specialties that are used in agriculture to treat the diseases of vegetal species, to protect them from adverse biological species or to regulate their life cycle.

By "water soluble polymer" we mean a polymer which is soluble in water at a concentration of at least 1% by weight (distilled water, 20° C.).

By "solid" agrochemically active substance we mean an agrochemically active substance which is solid at room temperature.

By "water insoluble" or "not soluble in water" agrochemically active substance we mean an agrochemically active substance which is soluble in water for less than 20 g/l (distilled water, 20° C.).

Useful agrochemically active ingredient include herbicides, fungicides, insecticides, acaricides, plant growth regulators (fertilisers, adjuvants and water excluded), bactericides, nematocides, miticides, rodenticides, molluscicides, bird repellents.

Specific examples of herbicides include; substituted ureas such as Diuron, isoproturon, linuron; sulphonyl ureas, such as methsulfuron-methyl, and tribenuron-methyl; bis-carbamates, such as Desmedipham and Phenmmedipham; metamitron; quinmerac; chloridazon; propyzamide; diflufenican; metribuzin.

Specific examples of fungicides include thiocarbamates, particularly alkylenebis(dithiocarbamate)s, such as Maneb and Mancozeb; strobilurins such as azoxystrobin and kresoxim-methyl, dicarboximides such as iprodione; azoles such as propiconazole, difenoconazole and tebuconazole; fludioxonil; halophthalonitriles, such as chlorothalonil.

Specific examples of insecticides include benzoyl ureas such as Diflubenzuron; imidacloprid; carbamate, such as carbaryl.

Specific examples of acaricides include tetrazines, such as Clofentezine.

The agrochemically active ingredient is typically characterized by having high melting point, to avoid melting in the grinding process, that is melting point higher than 40° C., and, preferably, by having a very low solubility in water (<2000 ppm, distilled water, 20° C.), to reduce the risk of crystal growth during long term storage of the agrochemical composition or once diluted with water.

The aqueous agrochemical compositions containing at least one solid organic agrochemically active ingredient that is insoluble in water is advantageously in the form of stable aqueous suspension concentrate and it is generally diluted as necessary with water or other proper solvent just before use in field.

The aqueous suspension concentrate comprises from 50 g/l to 1100 g/l and more preferably from 200 g/l to 700 g/l, of agrochemically active ingredient and from 0.05 to 10% by weight, and more preferably from 0.5 to 8% by weight, of the water soluble polymer defined above.

The content of water in the suspension concentrate is typically from 20 to 80% by weight.

The carboxylated water soluble polymer, that acts as wetting and dispersing agent, is the characterizing feature of the aqueous agrochemical composition.

In the water soluble polymer at least 85 mole % of the monomer units derive from ethylenically unsaturated $C_3$-$C_5$ mono carboxylic acids, bi-carboxylic acids or anhydrides thereof that are selected among acrylic acid, methacrylic acid, maleic acid, fumaric acid, crotonic acid, itaconic acid and anhydrides thereof.

In the water soluble polymer preferably at least 85% by moles of the monomer units, and most preferably 100% by moles of the monomer units, derive from acrylic acid.

From 0 to 15% by moles of the monomer units of the carboxylated water soluble polymer derive from one or more non-carboxylated ethylenically unsaturated nonionic or ionic monomers.

Examples of such non-carboxylated monomers are amides, alkyl esters, with or without hydroxyl or amino groups in the ester radical, alcohols, sulfonic acids and ethers with ethylenically unsaturated radicals, olefins and styrene.

Specific examples of non-carboxylated monomers are acrylamide, methacrylamide, 2-acrylamido-2-methylpropanesulfonic acid, vinylsulfonic acid, allylsulfonic acid, vinylphosphonic acid, allylphosphonic acid, vinyl acetate, vinyl propionate, methyl acrylate and methacrylate, ethyl acrylate and methacrylate, hydroxyethyl acrylate and methacrylate, hydroxypropyl acrylate and methacrylate, dialkylaminoethyl acrylate and methacrylate, vinylglycol, allyl alcohol, ethylene, propylene, isobutylene, methyl vinyl ether, ethyl vinyl ether, isobutyl vinyl ether, styrene and butadiene.

Preferably, the non-carboxylated monomers are nonionic, and the sum of the ethylenically unsaturated $C_3$-$C_5$ mono carboxylic acids, bi-carboxylic acids or anhydrides thereof and the non-carboxylated monomers is 100% by moles, which improves the versatility of the water soluble polymer.

With the term "polystyrylphenol" we mean distryrylphenol and tristyrylphenol, and also the analogue di- and tri-α-methylstyrylphenol.

With the term "polyalkoxylated" we mean alkoxylated with more than one mole of at least one alkylene oxide, which is typically ethylene oxide, propylene oxide or butylene oxide.

According to particularly preferred embodiments, the carboxylic acid groups of the water soluble polymer are esterified with at least one polyalkoxylated polystyrylphenol which is polyethoxylated tristyrylphenol, most preferably they are esterified with at least one tristyrylphenol which is polyethoxylated with from 10 to 30 moles of ethylene oxide; from 5 to 55%, preferably from 8% to 30%, most preferably from 10% to 15%, of the carboxylic acid groups of the water soluble polymer are esterified with the polyalkoxylated polystyrylphenol.

Especially in these preferred embodiment the water soluble polymer has a remarkable versatility, showing excellent wetting and dispersing performances on different agrochemically active ingredients, even in concentrated form.

By different agrochemically active ingredients we mean agrochemically active ingredients that are different not only in their chemical structure, but also in their lipophilicity. In agrochemistry, the logarithm of the ratio of the concentrations of the unionized solute in two solvents, respectively octanol and water, is used as an index of the pesticide lipophilicity, and is called log $P_{octanol/water}$, or log POW, or simply log P.

The water soluble polymer of the invention thus consents the preparation of aqueous suspension concentrates containing from 50 to 1100 g/l of at least one pesticide having log POW from −1.5 to +6.

Aqueous suspension concentrates containing of agrochemical active ingredients, at least two of them differing in the log POW of more than 1.0 unit, and even of more than 1.5 units, are therefore another object of the invention.

Preferably the carboxylic acid groups of the water soluble carboxylated polymer are partially or totally salified with inorganic bases, such as sodium, potassium or ammonium hydroxide, or organic bases.

More preferably the base is organic and is a primary, secondary or tertiary amine. Example of useful amines are triethanolamine, monoethanolamine, diethanolamine, monoethylamine, diethylamine, cyclohexylamine, The useful carboxylated water soluble polymers may be obtained by two different synthetic methods.

According to the first and preferred synthetic method, the carboxylated water soluble polymer is prepared by i) radically polymerizing at least 85% by moles of ethylenically unsaturated $C_3$-$C_5$ mono carboxylic acids, bi-carboxylic acids or anhydride thereof and from 0 to 15% by moles of one or more non-carboxylated ethylenically unsaturated monomers, ii) esterifying the thus obtained polymer with from 5% to 55% equivalents, based on the carboxylic acid groups of the polymer, of a polyalkoxylated polystyrylphenol, to obtain a post-esterified water soluble polymer.

According to the second synthetic method, the carboxylated water soluble polymer is prepared by radically polymerizing from 0.8 to 19 equivalents of ethylenically unsaturated $C_3$-$C_5$ mono carboxylic acids, bi-carboxylic acids or anhydride thereof, with 1 equivalent of one or more ethylenically unsaturated monomer derived from a polyalkoxylated polystyrylphenol, and optionally with one or more non-carboxylated ethylenically unsaturated monomers, to obtain a copolymerized water soluble polymer according to the invention.

The first method is preferred because it involves the use of lower amounts of solvent, typically of water, and especially because it provides a better performing dispersant.

Without being bound to any theory, it is supposed that the better performance may derive from the more uniform substitution of the ester groups along the backbone of the water soluble polymer. Actually, the ethylenically unsaturated $C_3$-$C_5$ mono carboxylic acids, bi-carboxylic acids, or anhydride thereof, and the monomers derived from a polyalkoxylated polystyrylphenol possess different polymerization parameters, including different reactivity and mobility and this fact alone possibly leads to a different, less homogeneous distribution of the ester groups of the copolymerized water soluble polymer than in the post-esterified water soluble polymer.

Especially in case where the degree of esterification is close to the lower useful level according to the invention, a significant portion of the completely non esterified non performing polymer chains are even expected to be present in the copolymerized water soluble polymer.

Moreover, the copolymerized water soluble polymer has a broader molecular weight distribution, higher amount of residual monomers and low molecular weight polymers, which cannot be removed economically.

In step i) of the first synthetic method, the ethylenically unsaturated $C_3$-$C_5$ mono carboxylic acids, bi-carboxylic acids or anhydride thereof, that are selected among acrylic acid, methacrylic acid, maleic acid, fumaric acid, crotonic acid, itaconic acid and anhydride thereof, and optionally the one or more non-carboxylated ethylenically unsaturated monomers are radically polymerized in the presence of polymerization initiators to obtain a polymer which has weight average molecular weight between 500 and 50,000 dalton, preferably from 500 to 10,000 dalton, most preferably from 1,000 to 8,000 dalton, as determined by Gel Permeation Chromatography with standards of polyacrylic acid.

The polymerization of step i) of the first synthetic method and the polymerization of the second synthetic method can be performed by all known methods of solution, bulk, precipitation or emulsion polymerization.

Polymerization in solution, and particularly polymerization in aqueous solution is the preferred method.

If the polymers are prepared by solution or precipitation polymerization, the solvent may be water, a mixture of water and up to 60% by weight, based on the mixture, of an OH-containing solvent which is selected from among C1-C4-alkanols, C2-C10-alkylene glycols, in which the alkylene chain may be interrupted by one or more non-adjacent oxygen atoms and monoethers of the C2-C10-alkylene glycols with C1-C4-alkanols. Examples of suitable OH-containing solvents are methanol, ethanol, isopropanol, n-butanol, ethylene glycol, diethylene glycol, methyl diglycol, dipropylene glycol, butyl glycol, butyl diglycol, triethylene glycol, the methylethers of said glycols and also oligomers of ethylene oxide containing from 4 to 6 ethylene oxide units, oligomers of propylene oxide containing from 3 to 6 propylene oxide units and also polyethylene glycol-polypropylene glycol cooligomers.

Furthermore, the aqueous reaction medium can further comprise other water-miscible solvents such as acetone, methyl ethyl ketone, tetrahydrofuran, dioxane, N-methylpyrrolidone, dimethylformamide, etc.

According to a particularly preferred embodiment, the polymerization is carried out in water as the sole solvent.

If step i) is performed by solution or precipitation polymerization, the solvent may also be an organic inert solvent. Suitable solvents include cyclic ethers such as tetrahydrofuran or dioxane, ketones such as acetone, methyl ethyl ketone, cyclohexanone, esters of aliphatic carboxylic acids with C1-C4-alkanols, e.g. ethyl acetate or n-butyl acetate, aromatic hydrocarbons such as toluene, xylenes, cumene, chlorobenzene, ethylbenzene, industrial mixtures of alkylaromatics, cyclohexane and industrial mixtures of aliphatics.

The polymerization initiators used for the free-radical polymerization are preferably soluble in the reaction medium. They are used in amounts of up to 30% by weight, preferably from 0.05 to 15% by weight, particularly preferably from 0.2 to 8% by weight, based on the monomers used in the polymerization.

If the polymerization is carried out in a water-containing solvent, preference is given to using water-soluble polymerization initiators such as sodium persulfate, potassium persulfate, ammonium persulfate, hydrogen peroxide, tert-butyl hydroperoxide, 2,2'-azobis(2-amidinopropane)dihydrochloride. The initiators are used either alone or in admixture, e.g. mixtures of hydrogen peroxide and sodium persulfate.

The known redox initiator systems can also be used as polymerization initiators. Such redox initiator systems comprise at least one peroxide-containing compound in combination with a redox coinitiator, for example sulfur compounds having a reducing action, e.g. bisulfites, sulfites, thiosulfates, dithionites and tetrathionates of alkali metals and ammonium compounds, sodium hydroxymethanesulfinate dihydrate and thiourea. Thus, it is possible to use combinations of peroxodisulfates with alkali metal or ammonium hydrogen sulfites, e.g. ammonium peroxodisulfate and ammonium disulfite. The weight ratio of peroxide-containing compounds to the redox coinitiators is preferably from 30:1 to 0.05:1.

In combination with the initiators or the redox initiator systems, it is possible to additionally use transition metal catalysts such as iron, nickel, cobalt, manganese, copper, vanadium or chromium salts, e.g. iron(II) sulfate, cobalt(II) chloride, nickel(II) sulfate, copper(I) chloride, manganese (II) acetate, vanadium(III) acetate, manganese(II) chloride. Based on the monomers, these transition metal salts are usually used in amounts of from 0.1 ppm to 1000 ppm. Thus, it is possible to use combinations of hydrogen peroxide with iron(II) salts, e.g. from 0.5 to 30% of hydrogen peroxide and from 0.1 to 500 ppm of Mohr's salt.

For the polymerization in a nonaqueous medium, preference is given to using initiators such as dibenzoyl peroxide, dicyclohexyl peroxydicarbonate, dilauryl peroxide, methyl ethyl ketone peroxide, acetylacetone peroxide, tert-butyl hydroperoxide, cumene hydroperoxide, tert-butyl perneodecanoate, tert-amyl perpivalate, tert-butyl perpivalate, tert-butyl perneohexanoate, tert-butyl per-2-ethylhexanoate, tert-butyl perbenzoate, azobisisobutyronitrile, 2,2'-azobis(N,N'-dimethyleneisobutyramidine)dihydrochloride, 4,4'-azobis (4-cyanovaleric acid). In combination with these initiators, it is possible to use reducing agents such as benzoin, dimethylaniline, ascorbic acid and, if desired, complexes and salts of transition metals which are soluble in the reaction medium.

The polymerization reaction is preferably carried out at from 50 to 160° C. and very particularly preferably from 80 to 120° C. Preference is given to carry out the reaction with exclusion of oxygen, preferably in nitrogen atmosphere. The polymerization is generally carried out at atmospheric pressure, but it is possible to employ lower or higher pressures, particularly when the polymerization temperatures employed are above the boiling point of the solvent.

To set the desired molecular weight of the polymers, as indicated above, it may be necessary to carry out the polymerization in the presence of a molecular weight regulator, ie. a customary chain-terminating substance. Suitable molecular weight regulators include, for example, formaldehyde, acetaldehyde, propionaldehyde, n-butyraldehyde, isobutyraldehyde, formic acid, ammonium formate, hydroxylamine and its sulfate, chloride or phosphate; SH-containing compounds such as thioglycolic acid, mercaptopropionic acid, mercaptoethanol, mercaptopropanol, mercaptobutanols, mercaptohexanol, thiomaleic acid, thiophenol, 4-tert-butylthiophenol, n-dodecylmercaptan, tert-dodecylmercaptan.

Further examples of polymerization regulators are allyl alcohol, butenol, isopropanol, n-butanol, isobutanol, glycol, glycerol, pentaerythritol.

If the use of polymerization regulators is required, they are employed in amounts of up to 20% by weight, based on the monomers. Polymerization is preferably carried out in the presence of from 0.5 to 15% by weight of an SH-containing polymerization regulator, based on the monomers.

The reaction conditions of the esterification step ii) of the first synthetic method are known in the field to those skilled in the art. Preferably, the neat polyalkoxylated polystyrylphenol is mixed with the reaction mixture obtained from step i); if water is present, it is distilled off and esterification is carried out by addition of an esterification catalyst, typically p-toluenesulphonic acid, heating the mixture between 100° C. and 200° C. and distilling off the reaction water, if any.

The amount of polyalkoxylated polystyrylphenol in step ii) is calculated by titrating the acid groups of the polymer obtained from step i) and from the desired final esterification degree. Analogously, the completion of the reaction is monitored by titrating the acid groups of the polymer, till the theoretical value (calculated from the titrated initial acid groups of the polymer and the amount of polyalkoxylated polystyrylphenol) is reached.

The ethylenically unsaturated monomers derived from polyalkoxylated polystyrylphenol and used to prepare the polymerized water soluble polymer according to the second synthetic method are typically the mono- or di-ester of polyalkoxylated polystyrylphenol with (meth)acrylic, acid, itaconic acid, crotonic acid, maleic acid, fumaric acid.

The water soluble polymer obtained from both the first method and the second method is preferably reacted with a base to partially or totally salify the carboxylic acid groups and enhance its solubility in water.

The base may be an inorganic base, such as sodium, potassium or ammonium hydroxide, or organic.

Preferably the base is organic and is a primary, secondary or tertiary amine. Example of useful amines are triethanolamine, monoethanolamine, diethanolamine, monoethylamine, diethylamine, cyclohexylamine.

The water soluble polymer may be diluted, before or after the salification, with a suitable solvent; glycols, and especially monopropyleneglycol, are the preferred diluents.

The suspension concentrate of the invention are usually prepared by diluting in water the water soluble polymer, adding the pesticide and milling.

The aqueous suspension concentrate may also comprise an anti-settling agent and an antifreeze.

Anti-settling agents are typically added to suspension concentrates to prevent or at least reduce the settling of particles during storage. They are generally water soluble polymers which impart some viscosity to water and can build up a structure or gel where the particles remain trapped and do not sag. Examples of water soluble anti-settling agents are xanthan gum, cellulose derivatives, e.g. hydroxyethylcellulose, natural gums, modified starches, polyvinyl alcohol, poly(ethylene oxide. Among these, xanthan gum is by far the most used anti-settling agent). Along with water soluble polymer thickener, fine dispersed clays (bentonite, attapulgite) and high surface silicas may also be used to help the stability of the suspension.

The anti-settling agents usually amount for about 0.05 to 1% by weight of the suspension concentrate.

The agrochemical compositions of the invention may further contain one or more additives with different functions, such as:
fertilisers or micronutrients;
surfactants;
wetting agents;
crystal growth inhibitors
other products, such as anti-foam agents, colorants, stabilisers and buffers;
the additives normally used in agrochemical composition.

The agrochemical compositions of the invention advantageously do not contain any other wetting or dispersing agent, because the carboxylated water soluble polymer of the invention is perfectly performs both the functions.

EXAMPLES

The following products have been used in the synthesis:
PA1=polyacrylic acid in water, having $MW_w$ of about 2,000 dalton as determined by GPC with polyacrylic standard.
PA2=polyacrylic acid in water, having $MW_w$ of about 7,000 dalton as determined by GPC with polyacrylic standard.
TSP=20 moles ethoxylated tristyrylphenol
nP=20 moles ethoxylated 4-n-nonylphenol
CS=25 moles ethoxylated cetylstearyl alcohol
Preparation of the Water Soluble Polymers.
Preparation of Water Soluble Polymer 1.

In a reaction vessel equipped with heating, stirrer, thermometer, a system of introduction of the reagents, such reaction vessel connected to a cooler provided of collector of water, 304.0 g of acrylic polymer PA1 and 296.0 g of esterifying agent TSP are added. The reaction mixture is slowly heated to 130° C. under stirring and nitrogen flow until all the dilution water of acrylic acid polymer is distilled. After that, at the temperature of about 130° C., p-toluenesulphonic acid monohydrate is added. The temperature is set to 180° C. The reaction mixture is maintained at the reaction temperature until the acid number reaches the value indicate in Table 1.

At this point, the reaction mixture is cooled to 100° C. and, under stirring, 302.4 g of monopropylene glycol and 201.6 g of distilled water are slowly added.

The reaction mixture is maintained under stirring until the product becomes homogeneous.

At the temperature of about 60° C. 150 g of triethanolamine are added to bring the pH of the 1% water solution of the resulting composition to about 7 (Water soluble polymer 1, 50 wt % a.m.).

Analogously, the Water soluble polymers 2-8 (50 wt % a.m.), 9 (85 wt % a.m.) and 10 (80 wt % a.m) were prepared, with the reactants detailed in Table 1. Table 1 summarises the preparation and chemical structure of the water soluble polymers.

TABLE 1

| WSP | PA | % E | E | Acid No. | E (g) | PA (g) | MPG (g) | Water (g) | TEA (g) |
|---|---|---|---|---|---|---|---|---|---|
| 1 | PA1 | 12.5 | TSP | 203 | 296.0 | 304.0[1] | 302.4 | 201.6 | 150.0 |
| 2* | PA1 | 12.5 | nP | 203 | 196.8 | 203.2[2] | 252.0 | 168.0 | 120.0 |
| 3 | PA1 | 6.2 | TSP | 318 | 262.4 | 537.6[2] | 540.0 | 360.0 | 350.0 |
| 4 | PA1 | 25.0 | TSP | 105 | 206.5 | 143.5[3] | 168.8 | 112.5 | 60.0 |
| 5 | PA2 | 25.0 | TSP | 106 | 233.3 | 116.6[4] | 175.4 | 117.0 | 60.0 |
| 6* | PA1 | 12.5 | CS | 190 | 181.2 | 168.8[2] | 222.0 | 148.0 | 100.0 |
| 7 | PA1 | 50.0 | TSP | 39 | 260.0 | 90.0[3] | 120.4 | 80.2 | 17.0 |
| 8 | PA2 | 50.0 | TSP | 40 | 280.0 | 70.0[4] | 168.8 | 112.5 | 60.0 |
| 9* | PA1 | 75.0 | TSP | 14 | 427.0 | 73.0[1] | 15.8 | 31.5 | 12.0 |
| 10* | PA2 | 75.0 | TSP | 14 | 342.8 | 57.2[4] | 17.6 | 17.6 | 7.5 |

*comparative
WSP = water soluble polymer
PA = polyacrylic acid
% E = % of esterified carboxylic acid groups in the WSP
E = esterfying agent
Acid No. = acid number expressed in mg KOH/g
(g) = grams
MPG = monopropylene glycol
TEA = triethanolamine 98%
dry matter of the PA: [1] 54 wt %; [2] 55% wt % [3] 42% wt % [4] 53 wt %

Preparation of the Suspension Concentrates.

The Water soluble polymers 1-10 were used to prepare suspension concentrates of agrochemically active ingredients.

The suspension concentrates were prepared with the ingredient listed in Table 2-9 and according to the following procedure:
1) monopropylene glycol (MPG) and water soluble polymer are mixed together to form a homogeneous solution in a beaker
2) water is added and the solution is stirred till is limpid
3) the agrochemically active ingredient is added
4) the obtained suspension is mixed by using an high shear mixer (Ultra Turrax) for at least ten minutes
5) the suspension is milled with DYNO®-MILL KD till particle size of active ingredients is less than 5 microns, measured as D(90) (see below).
6) the suspension concentrate is completed by adding a xanthan gum to get the a Brookfield viscosity from 700 to 1800 mPa*s at 20 rpm, 20° C. and mixing for at least one hour (when possible).

The following characteristics of the suspension concentrates were measured:
Brookfield Viscosity, in mPas at 20 rpm, 20° C., with a Brookfield Digital Model DV-I;
Particle diameter, D(90) in micron, corresponding to 90% of the cumulative distribution by volume as defined by standard method ISO 13320-1, with a Malvern Mastersizer Hydro 2000S;
Spontaneity, according to the test method MT 160, CIPAC Handbook (Spontaneity of dispersion of suspension concentrates); it is based on the preparation of 250 ml of a mixture of the suspension concentrate and water, mixed with only one inversion of the measuring cylinder. After standing 5 minutes under defined conditions the top nine-tenths is removed, and the remaining tenth assayed chemically, gravimetrically or by solvent extraction. The method gives an index of the immediate homogeneity of the diluted suspension concentrate. Complete immediate homogeneity corresponds to 100%.
Suspensibility, according to the test method MT 161, CIPAC Handbook (Suspensibility of aqueous suspension concentrates); it involves preparing 250 ml of aqueous diluted suspension concentrate mixed with thirty inversions of the measuring cylinder, allowing it to stand for a specified time in the cylinder (1 hour in the Examples) under defined conditions, and removing the top nine-tenths. The remaining tenth is then assayed essayed either chemically, gravimetrically or by solvent extraction. The method gives an index of the stability of the homogeneity of the diluted suspension concentrate over time. Complete stability of the homogeneity corresponds to 100%.
Separation of a water phase in the suspension concentrate as such, as percentage in volume (the presence of a supernatant water layer on the top of the suspension is visually observed);
Sedimentation and agglomeration of solids in the suspension concentrate as such (a soft cake or claying of active ingredient at the bottom of the bottle containing the suspension is visually observed).

The storage stability of the suspension concentrates is evaluated by storing them at 20° C. and 54° C. for two (according to CIPAC 1-MT 46.1.3) or four weeks, and repeating the relevant tests, as detailed in the tables here below.

The data obtained are reported in the Tables 2a-e to 9a-e.

The asterisk aside the suspension concentrate name means "comparative".

TABLE 2

| | Metamitron[1] 500 | | |
| --- | --- | --- | --- |
| | M-SC1 | M-SC4 | M-SC10*[2] |
| Metamitron (98% tech.) | 43.4 | 43.4 | 43.4 |
| MPG | 5 | 5 | 5 |
| WSP 1 | 1.5 | | |
| WSP 4 | | 1.5 | |
| WSP 10 | | | 1.5 |
| XG | 10 | 10 | — |
| Antifoam | 0.5 | 0.5 | 0.5 |
| Acid | 0.6 | 0.6 | 0.6 |
| H$_2$O dist | 39 | 39 | 39 |

[1] log P = 0.83
*[2] The mixture could not be milled, too viscous.
XG = xanthan gum 2 wt % in water
Acid = citric acid 50 wt % in water
H$_2$O dist = distilled water TABLE 2a

| | Viscosity | | |
| --- | --- | --- | --- |
| | M-SC1 | M-SC4 | M-SC10* |
| V$_i$ | 1300 | 1350 | nd |
| V$_{f20}$ (mPas) | 1280 | 1292 | nd |
| V$_{f54}$ (mPas) | 1270 | 1280 | nd |

V$_i$ – Brookfield Viscosity
V$_{f20}$ – Brookfield Viscosity, after 4 weeks at 20° C.
V$_{f54}$ – Brookfield Viscosity, after 4 weeks at 54° C.

TABLE 2b

| | Granulometry | | |
| --- | --- | --- | --- |
| | M-SC1 | M-SC4 | M-SC10* |
| D (90) (micron) | 4.32 | 4.5 | nd |

TABLE 2c

| Spontaneity | M-SC1 | M-SC4 | M-SC10* |
| --- | --- | --- | --- |
| Spo$_i$ (%) | 98 | 98 | nd |
| Spo$_{f54}$ (%) | 92 | 96 | nd |

Spo$_i$ = Spontaneity
Spo$_{f54}$ = Spontaneity, after two weeks at 54° C.

TABLE 2d

| | Suspensibility | | |
| --- | --- | --- | --- |
| | M-SC1 | M-SC4 | M-SC10* |
| Sus$_i$ (%) | 92 | 96 | nd |
| Sus$_{f54}$ (%) | 96 | 95 | nd |

Sus$_i$ – Suspensibility
Sus$_{f54}$ – Suspensibility, after two weeks at 54° C.

TABLE 2e

| Separation | M-SC1 | M-SC4 | M-SC10* |
|---|---|---|---|
| $Sep_i$ (%) | 0 | 0 | nd |
| $Sep_{f20}$ (%) | 0 | 0 | nd |
| $Sep_{f54}$ (%) | 3.0 | 3.2 | |

$Sep_i$ = Separation (v/v)
$Sep_{f20}$ = Separation (v/v), after four weeks at 20° C.
$Sep_{f54}$ = Separation (v/v), after four weeks at 54° C.

The suspension concentrates of Table 2, except the comparative M-SC10, did not show any sedimentation or agglomeration of solids, nor immediately, nor after 4 weeks at 54° C.

TABLE 3

| Chlorothalonil[1] | C-SC1 | C-SC2* | C-SC4 | C-SC6*[2] | C-SC9*[2] | C-SC10*[2] | C-A1* |
|---|---|---|---|---|---|---|---|
| Chlorothalonil (98% tech.) | 41 | 41 | 41 | 41 | 41 | 41 | 41 |
| MPG | 5 | 5 | 5 | 5 | 5 | 5 | 5 |
| WSP 1 | 2 | | | | | | |
| WSP 2 | | 2 | | | | | |
| WSP 4 | | | 2 | | | | |
| WSP 6 | | | | 2 | | | |
| WSP 9 | | | | | 2 | | |
| WSP 10 | | | | | | 2 | |
| PA1 | | | | | | | 1 |
| XG | 10 | 10 | 10 | — | — | — | 10 |
| Antifoam | 0.25 | 0.25 | 0.25 | 0.25 | 0.25 | 0.25 | 0.25 |
| H$_2$O dist | 41.75 | 41.75 | 41.75 | 41.75 | 41.75 | 41.75 | 42.75 |

[1] logP = 2.92
[2] the mixture exits semi-solid from the mill
XG = xanthan gum 2% in water
H$_2$O dist = distilled water

TABLE 3a

| Viscosity | C-SC1 | C-SC2* | C-SC4 | C-SC6* | C-SC9* | C-SC10* | C-A1* |
|---|---|---|---|---|---|---|---|
| Vi | 1150 | nd | 1120 | nd | nd | nd | 1135 |
| V$_{f20}$ (mPas) | 915 | nd | 900 | nd | nd | nd | nd |
| V$_{f54}$ (mPas) | 630 | nd | 635 | nd | nd | nd | nd |

Vi = Brookfield Viscosity
V$_{f20}$ = Brookfield Viscosity, after 4 weeks at 20° C.
V$_{f54}$ = Brookfield Viscosity, after 4 weeks at 54° C.

TABLE 3b

| Granulometry | C-SC1 | C-SC2* | C-SC4 | C-SC6* | C-SC9* | C-SC10* | C-A1* |
|---|---|---|---|---|---|---|---|
| D(90) (micron) | 4.29 | 4.30 | 4.02 | 2.46 | 3.80 | 3.60 | 3.02 |

TABLE 3c

| Spontaneity | C-SC1 | C-SC2* | C-SC4 | C-SC6* | C-SC9* | C-SC10* | C-A1* |
|---|---|---|---|---|---|---|---|
| Spo$_i$ (%) | 100 | 63 | 98 | 62 | 60 | 59 | 60 |
| Spo$_{f54}$ (%) | 98 | nd | 97 | nd | nd | nd | nd |

Spo$_i$ = Spontaneity
Spo$_{f54}$ = Spontaneity, after two weeks at 54° C.

TABLE 3d

| Suspensibility | C-SC1 | C-SC2* | C-SC4 | C-SC6* | C-SC9* | C-SC10* | C-A1* |
|---|---|---|---|---|---|---|---|
| Sus$_i$ (%) | 92 | 55 | 96 | nd | 30 | 26 | 30 |
| Sus$_{f54}$ (%) | 96 | nd | 95 | nd | nd | nd | nd |

Sus$_i$ = Suspensibility
Sus$_{f54}$ = Suspensibility, after two weeks at 54° C.

TABLE 3e

| Separation | C-SC1 | C-SC2* | C-SC4 | C-SC6* | C-SC9* | C-SC10* | C-A1* |
|---|---|---|---|---|---|---|---|
| Sep$_i$ (%) | 0 | 0 | 0 | nd | nd | nd | nd |
| Sep$_{f20}$ (%) | 0 | 0 | 0 | nd | nd | nd | nd |
| Sep$_{f54}$ (%) | 2 | 2 | 2.5 | nd | nd | nd | nd |

Sep$_i$ = Separation (v/v)
Sep$_{f20}$ = Separation (v/v), after four weeks at 20° C.
Sep$_{f54}$ = Separation (v/v), after four weeks at 54° C.

All the suspension concentrates of Table 3, except the comparative suspension concentrates, did not show any sedimentation or agglomeration of solids, nor immediately, nor after 4 weeks at 54° C.

TABLE 4

Azoxystrobin[1]

| | A-SC1 | A-SC4 | A-SC7 | A-SC8 |
|---|---|---|---|---|
| Azoxystrobin (98% tech.) | 23.4 | 23.4 | 23.4 | 23.4 |
| MPG | 10 | 10 | 10 | 10 |
| WSP 1 | 2 | | | |
| WSP 4 | | 2 | | |
| WSP 7 | | | 2 | |
| WSP 8 | | | | 2 |
| XG | 10 | 10 | 10 | 10 |
| Antifoam | 0.2 | 0.2 | 0.2 | 0.2 |
| H$_2$O dist | 54.4 | 54.4 | 54.4 | 54.4 |

[1] logP = 2.5

XG = xanthan gum 3% in water

H$_2$O dist = distilled water

TABLE 4a

Viscosity

| | A-SC1 | A-SC4 | A-SC7 | A-SC8 |
|---|---|---|---|---|
| V$_i$ (mPas) | 1145 | 1145 | 1200 | 1300 |
| V$_{f20}$ (mPas) | 1140 | 1140 | 1160 | 1190 |
| V$_{f54}$ (mPas) | 785 | 785 | 850 | 842 |

V$_i$ = Brookfield Viscosity

V$_{f20}$ = Brookfield Viscosity, after 4 weeks at 20° C.

V$_{f54}$ = Brookfield Viscosity, after 4 weeks at 54° C.

TABLE 4b

Granulometry

| | A-SC1 | A-SC4 | A-SC7 | A-SC8 |
|---|---|---|---|---|
| D (90) (micron) | 2.46 | 2.46 | 3.2 | 3.8 |

TABLE 4c

Spontaneity

| | A-SC1 | A-SC4 | A-SC7 | A-SC8 |
|---|---|---|---|---|
| Spo$_i$ (%) | 100 | 100 | 100 | 100 |
| Spo$_{f54}$ (%) | 98 | 98 | 100 | 100 |

Spo$_i$ = Spontaneity

Spo$_{f54}$ = Spontaneity, after two weeks at 54° C.

TABLE 4d

Suspensibility

| | A-SC1 | A-SC4 | A-SC7 | A-SC8 |
|---|---|---|---|---|
| Sus$_i$ (%) | 98 | 98 | 95 | 96 |
| Sus$_{f54}$ (%) | 98 | 98 | 96 | 94 |

Sus$_i$ = Suspensibility;

Sus$_{f54}$ = Suspensibility, after two weeks at 54° C.

TABLE 4e

Separation

| | A-SC1 | A-SC4 | A-SC8 | A-SC8 |
|---|---|---|---|---|
| Sep$_i$ (%) | 0 | 0 | 0 | 0 |
| Sep$_{f20}$ (%) | 0 | 0 | 0 | 0 |
| Sep$_{f54}$ (%) | 0 | 0 | 0 | 0 |

Sep$_i$ = Separation (v/v);

Sep$_{f20}$ = Separation (v/v), after four weeks at 20° C.

Sep$_{f54}$ = Separation (v/v), after four weeks at 54° C.

All the suspension concentrates of Table 4, did not show any sedimentation or agglomeration of solids, nor immediately, nor after 4 weeks at 54° C.

TABLE 5

Metamitron[1] + Quinmerac[2] + Chloridazone[3]

| | Mix1-SC1 |
|---|---|
| Metamitron (98% tech.) | 32.4 |
| Quinmerac (98% tech.) | 5.4 |
| Chloridazone (92% tech.) | 18.2 |
| WSP 1 | 5.5 |
| MPG | 4.9 |
| XG | 3 |
| Antifoam | 0.2 |
| H$_2$O dist | 30.4 |

[1] logP = 0.83

[2] logP = −1.11

[3] logP = 1.19

XG = xanthan gum 3% in water;

H$_2$O dist = distilled water

TABLE 5a

Viscosity

| | Mix1-SC1 |
|---|---|
| V$_i$ (mPas) | 1256 |
| V$_{f20}$ (mPas) | 1160 |
| V$_{f54}$ (mPas) | 1110 |

V$_i$ = Brookfield Viscosity

V$_{f20}$ = Brookfield Viscosity, after 4 weeks at 20° C.

V$_{f54}$ = Brookfield Viscosity, after 4 weeks at 54° C.

TABLE 5b

Granulometry

| | Mix1-SC1 |
|---|---|
| D(90) (micron) | 4.3 |

TABLE 5c

Spontaneity

| | Mix1-SC1 |
|---|---|
| Spo$_i$ (%) | 99 |
| Spo$_{f54}$ (%) | 99 |

Spo$_i$ = Spontaneity

Spo$_{f54}$ = Spontaneity, after two weeks at 54° C.

TABLE 5d

| Suspensibility | |
|---|---|
| | Mix1-SC1 |
| $Sus_i$ (%) | 98 |
| $Sus_{f54}$ (%) | 98 |

$Sus_i=$ Suspensibility
$Sus_{f54}=$ Suspensibility, after two weeks at 54° C.

TABLE 5e

| Separation | |
|---|---|
| | Mix1-SC1 |
| $Sep_i$ (%) | 0 |
| $Sep_{f20}$ (%) | 0 |
| $Sep_{f54}$ (%) | 2 |

$Sep_i=$ Separation (v/v);
$Sep_{f20}=$ Separation (v/v), after four weeks at 20° C.
$Sep_{f54}=$ Separation (v/v), after four weeks at 54° C.

The suspension concentrate of Table 5 did not show any sedimentation or agglomeration of solids, nor immediately, nor after 4 weeks at 54° C.

TABLE 6

| Propyzamide[1] + Diflufenican[2] | |
|---|---|
| | Mix2-SC1 |
| Propyzamide (98% tech.) | 38 |
| Diflufenican (99% tech.) | 3.7 |
| MPG | 7 |
| WSP 1 | 5.5 |
| MEA | 0.9 |
| XG | 3 |
| Preservative | 0.4 |
| Antifoam | 0.2 |
| $H_2O$ dist | 35.3 |

[1] logP = 3.1
[2] logP = 4.9
MEA = monoethyleneamine
XG = xanthan gum 3% in water
Preservative = Carbosan CD 40 from Lamberti SpA, IT
$H_2O$ dist = distilled water

TABLE 6a

| Viscosity | |
|---|---|
| | Mix2-SC1 |
| $V_i$ (mPas) | 910 |
| $V_{f20}$ (mPas) | 880 |
| $V_{f54}$ (mPas) | 525 |

$V_i=$ Brookfield Viscosity
$V_{f20}=$ Brookfield Viscosity, after 4 weeks at 20° C.
$V_{f54}=$ Brookfield Viscosity, after 4 weeks at 54° C.

TABLE 6b

| Granulometry | |
|---|---|
| | Mix2-SC1 |
| D(90) (micron) | 3.8 |

TABLE 6c

| Spontaneity | |
|---|---|
| | Mix2-SC1 |
| $Spo_i$ (%) | 98 |
| $Spo_{f54}$ (%) | 98 |

$Spo_i=$ Spontaneity
$Spo_{f54}=$ Spontaneity, after two weeks at 54° C.

TABLE 6d

| Suspensibility | |
|---|---|
| | Mix2-SC1 |
| $Sus_i$ (%) | 100 |
| $Sus_{f54}$ (%) | 100 |

$Sus_i=$ Suspensibility
$Sus_{f54}=$ Suspensibility, after two weeks at 54° C.

TABLE 6e

| Separation | |
|---|---|
| | Mix2-SC1 |
| $Sep_i$ (%) | 0 |
| $Sep_{f20}$ (%) | 0 |
| $Sep_{f54}$ (%) | 0 |

$Sep_i=$ Separation (v/v)
$Sep_{f20}=$ Separation (v/v), after four weeks at 20° C.
$Sep_{f54}=$ Separation (v/v), after four weeks at 54° C.

The suspension concentrate of Table 6 did not show any sedimentation or agglomeration of solids, nor immediately, nor after 4 weeks at 54° C.

TABLE 7

| Metamitron[1] 700 | | |
|---|---|---|
| | MM-SC1 | MM-SC3 |
| Metamitron (98% tech.) | 59 | 59 |
| MPG | 5 | 5 |
| WSP 1 | 4.3 | |
| WSP 4 | | 4.3 |
| XG | 4 | 4 |
| Antifoam | 0.2 | 0.2 |
| CGI | 2.0 | 2.0 |
| Acid | 0.6 | 0.6 |
| $H_2O$ dist | 24.9 | 24.9 |

[1] logP = 0.83
XG = xanthan gum 3% in water
CGI = Emulson AG TRN 14105, crystal growth inhibitor (from Lamberti SpA, IT)
Acid = citric acid 50% in water
$H_2O$ dist = distilled water

TABLE 7a

| Viscosity | | |
|---|---|---|
| | MM-SC1 | MM-SC3 |
| $V_i$ (mPas) | 1780 | 1770 |
| $V_{f20}$ (mPas) | 1700 | 1680 |
| $V_{f54}$ (mPas) | 1645 | 1650 |

$V_i$ = Brookfield Viscosity
$V_{f20}$ = Brookfield Viscosity, after 4 weeks at 20° C.
$V_{f54}$ = Brookfield Viscosity, after 4 weeks at 54° C.

TABLE 7b

| Granulometry | | |
|---|---|---|
| | MM-SC1 | MM-SC3 |
| D(90) (micron) | 4.5 | 4.3 |

TABLE 7c

| Spontaneity | | |
|---|---|---|
| | MM-SC1 | MM-SC3 |
| $Spo_i$ (%) | 98 | 96 |
| $Spo_{f54}$ (%) | 100 | 98 |

$Spo_i$ = Spontaneity
$Spo_{f54}$ = Spontaneity, after two weeks at 54° C.

TABLE 7d

| Suspensibility | | |
|---|---|---|
| | MM-SC1 | MM-SC3 |
| $Sus_i$ (%) | 99 | 96 |
| $Sus_{f54}$ (%) | 98 | 97 |

$Sus_i$ = Suspensibility
$Sus_{f54}$ = Suspensibility, after two weeks at 54° C.

TABLE 7e

| Separation | | |
|---|---|---|
| | MM-SC1 | MM-SC3 |
| $Sep_i$ (%) | 0 | 0 |
| $Sep_{f20}$ (%) | 0 | 0 |
| $Sep_{f54}$ (%) | 2.0 | 2.5 |

$Sep_i$ = Separation (v/v)
$Sep_{f20}$ = Separation (v/v), after four weeks at 20° C.
$Sep_{f54}$ = Separation (v/v), after four weeks at 54° C.

The suspension concentrates of Table 7 did not show any sedimentation or agglomeration of solids, nor immediately, nor after 4 weeks at 54° C.

TABLE 8

| Metribuzin[1] | |
|---|---|
| | Mz-SC1 |
| Metribuzin (95% tech.) | 52.6 |
| WSP 1 | 3 |
| MPG | 5 |
| Antifoam | 0.2 |

TABLE 8-continued

| Metribuzin[1] | |
|---|---|
| | Mz-SC1 |
| XG | 10 |
| $H_2O$ dist | 29.2 |

[1] logP = 1.6
MEA = monoethyleneamine
XG = xanthan gum 2% in water
$H_2O$ dist = distilled water

TABLE 8a

| Viscosity | |
|---|---|
| | Mz-SC1 |
| $V_i$ (mPas) | 1710 |
| $V_{f20}$ (mPas) | 1680 |
| $V_{f54}$ (mPas) | 1598 |

$V_i$ = Brookfield Viscosity
$V_{f20}$ = Brookfield Viscosity, after 4 weeks at 20° C.
$V_{f54}$ = Brookfield Viscosity, after 4 weeks at 54° C.

TABLE 8b

| Granulometry | |
|---|---|
| | Mz-SC1 |
| D(90) (micron) | 3.9 |

TABLE 8c

| Spontaneity | |
|---|---|
| | Mz-SC1 |
| $Spo_i$ (%) | 98 |
| $Spo_{f54}$ (%) | 96 |

$Spo_i$ = Spontaneity
$Spo_{f54}$ = Spontaneity, after two weeks at 54° C.

TABLE 8d

| Suspensibility | |
|---|---|
| | Mz-SC1 |
| $Sus_i$ (%) | 99 |
| $Sus_{f54}$ (%) | 98 |

$Sus_i$ = Suspensibility
$Sus_{f54}$ = Suspensibility, after two weeks at 54° C.

TABLE 8e

| Separation | |
|---|---|
| | Mz-SC1 |
| $Sep_i$ (%) | 0 |
| $Sep_{f20}$ (%) | 0 |
| $Sep_{f54}$ (%) | 3 |

$Sep_i$ = Separation (v/v)
$Sep_{f20}$ = Separation (v/v), after four weeks at 20° C.
$Sep_{f54}$ = Separation (v/v), after four weeks at 54° C.

The suspension concentrate of Table 8 did not show any sedimentation or agglomeration of solids, nor immediately, nor after 4 weeks at 54° C.

TABLE 9

Difenoconazole[1] + Fluodioxony[2] + Imidacloprid[3]

|  | Mix3-SC1 |
|---|---|
| Difenoconazole (96% tech.) | 2.47 |
| Fluodioxonyl (95% tech.) | 2.47 |
| Imidacloprid (95% tech.) | 30.5 |
| WSP 1 | 10 |
| MPG | 6.76 |
| Red Neoprint | 7.5 |
| XG | 4 |
| Antifoam | 0.5 |
| H$_2$O dist | 35.8 |

[1]logP = 4.2
[2]logP = 4.12
[3]logP = 0.57
Red Neoprint = pigment from Lamberti SpA, IT
XG = xanthan gum 3% in water
H$_2$O dist = distilled water TABLE 9a Viscosity

|  | Mix3-SC1 |
|---|---|
| $V_i$ (mPas) | 1720 |
| $V_{f20}$ (mPas) | 1654 |
| $V_{f54}$ (mPas) | 1490 |

$V_i$= Brookfield Viscosity
$V_{f20}$= Brookfield Viscosity, after 4 weeks at 20° C.
$V_{f54}$= Brookfield Viscosity, after 4 weeks at 54° C.

TABLE 9b

Granulometry

|  | Mix3-SC1 |
|---|---|
| D(90) (micron) | 4.3 |

TABLE 9c

Spontaneity

|  | Mix3-SC1 |
|---|---|
| Spo$_i$ (%) | 97 |
| Spo$_{f54}$ (%) | 95 |

Spo$_i$= Spontaneity
Spo$_{f54}$= Spontaneity, after two weeks at 54° C.

TABLE 9d

Suspensibility

|  | Mix3-SC1 |
|---|---|
| Sus$_i$ (%) | 99 |
| Sus$_{f54}$ (%) | 98 |

Sus$_i$= Suspensibility
Sus$_{f54}$= Suspensibility, after two weeks at 54° C.

TABLE 9e

Separation

|  | Mix3-SC1 |
|---|---|
| Sep$_i$ (%) | 0 |
| Sep$_{f20}$ (%) | 0 |
| Sep$_{f54}$ (%) | 0 |

Sep$_i$= Separation (v/v)
Sep$_{f20}$= Separation (v/v), after four weeks at 20° C.
Sep$_{f54}$= Separation (v/v), after four weeks at 54° C.

The suspension concentrate of Table 9 did not show any sedimentation or agglomeration of solids, nor immediately, nor after 4 weeks at 54° C.

The invention claimed is:

1. An agrochemical aqueous compositions comprising:
   at least one organic agrochemically active ingredient that is insoluble in water, and
   as a dispersing agent, a carboxylated water soluble polymer wherein:
   a) at least 85% by moles of monomer units derive from ethylenically unsaturated C$_3$-C$_5$ mono carboxylic acids, bi-carboxylic acids or anhydrides thereof and from 0 to 15% by moles of monomer units derive from one or more non-carboxylated ethylenically unsaturated monomers, and
   b) from 5% to 55% of carboxylic acid groups of the carboxylated water soluble polymer are esterified with at least one polyalkoxylated polystyrylphenol.

2. The agrochemical aqueous composition of claim 1 wherein from 0 to 15% by moles of the monomer units derive from one or more nonionic non-carboxylated ethylenically unsaturated monomers.

3. The agrochemical aqueous composition of claim 1 wherein 100% of the monomer units derive from ethylenically unsaturated C$_3$-C$_5$ mono carboxylic acids, bi-carboxylic acids or anhydrides thereof.

4. The agrochemical aqueous composition of claim 3 wherein at least 85% by moles of the monomer units derive from acrylic acid.

5. The agrochemical aqueous composition of claim 4 wherein 100% by moles of the monomer units derive from acrylic acid.

6. The agrochemical aqueous composition of claim 1 wherein the carboxylic acid groups of the carboxylated water soluble polymer are esterified with a polyalkoxylated polystyrylphenol which is a polyethoxylated tristyrylphenol.

7. The agrochemical aqueous composition of claim 6 wherein the tristyrylphenol is polyethoxylated with from about 10 to about 30 moles of ethylene oxide.

8. The agrochemical aqueous composition of claim 1 wherein from 8% to 30% of the carboxylic acid groups of the carboxylated water soluble polymer are esterified.

9. The agrochemical aqueous composition of claim 1 wherein the carboxylated water soluble polymer is prepared by:
   i) radically polymerizing the at least 85% by moles of the ethylenically unsaturated C$_3$-C$_5$ mono carboxylic acids, bi-carboxylic acids or anhydrides thereof and from 0 to 15% by moles of one or more non-carboxylated ethylenically unsaturated monomers to form a carboxylated polymer, and
   ii) esterifying the carboxylated polymer with from 5% to 55% of equivalents, based on the carboxylic acid groups of the polymer, of a polyalkoxylated polystyrylphenol.

10. The agrochemical aqueous composition of claim 9 wherein the carboxylic acid groups of the water soluble polymer are partially or totally salified.

11. The agrochemical aqueous composition of claim 1 wherein the agrochemical aqueous composition is a suspension concentrate comprising from 50 to 1100 g/l of the at least one agrochemically active ingredient.

12. The agrochemical aqueous composition of claim 11 wherein the at least one agrochemical active ingredient has a log POW of from −1.5 to 6.0.

13. The agrochemical aqueous composition of claim 11 comprising more than one agrochemical active ingredients, at least two of them differing in log POW by more than 1.0 units.

14. The agrochemical aqueous composition of claim 4 wherein the carboxylated water soluble polymer is a polyacrylic acid having MWw of about 2,000 dalton as determined by GPC with a polyacrylic standard.

15. The agrochemical aqueous composition of claim 14 wherein from 5% to 55% of carboxylic acid groups of the polyacrylic are esterified with at least one polyalkoxylated polystyrylphenol.

16. The agrochemical aqueous composition of claim 15 wherein 12.5% of the carboxylic acid groups of the polyacrylic are esterified with 20 moles ethoxylated tristyrylphenol.

17. A carboxylated water soluble polymer comprising a polymer prepared by:
   i) radically polymerizing at least 85% by moles of ethylenically unsaturated $C_3$-$C_5$ mono carboxylic acids, bi-carboxylic acids or anhydrides thereof and from 0 to 15% by moles of one or more noncarboxylated ethylenically unsaturated monomers to produce a carboxylated water soluble polymer, and
   ii) esterifying the carboxylated water soluble polymer with from 5% to 55% of equivalents, based on the carboxylic acid groups of the polymer, of a polyalkoxylated polystyrylphenol, wherein:
   a) at least 85% by moles of monomer units derive from ethylenically unsaturated $C_3$-$C_5$ mono carboxylic acids, bi-carboxylic acids or anhydride thereof and from 0 to 15% by moles of monomer units derive from one or more non-carboxylated ethylenically unsaturated monomers, and
   b) from 5% to 55% of carboxylic acid groups of the polymer are esterified with at least one polyalkoxylated polystyrylphenol.

18. The carboxylated water soluble polymer of claim 17 wherein from 0 to 15% by moles of the monomer units derive from one or more nonionic noncarboxylated ethylenically unsaturated monomers.

19. The carboxylated water soluble polymer of claim 17 wherein 100% by moles of the monomer units derive from ethylenically unsaturated $C_3$-$C_5$ mono carboxylic acids, bi-carboxylic acids or anhydrides thereof.

20. The carboxylated water soluble polymer of claim 19 wherein at least 85% by moles of the monomer units derive from acrylic acid.

21. The carboxylated water soluble polymer of claim 20 wherein 100% by moles of the monomer units derive from acrylic acid.

22. The carboxylated water soluble polymer of claim 17 wherein the carboxylic acid groups of the water soluble polymer are esterified with a polyalkoxylated polystyrylphenol which is tristyrylphenol polyethoxylated with from 10 to 30 moles of ethylene oxide.

23. The carboxylated water soluble polymer of claim 17 wherein from 8% to 30% of the carboxylic acid groups are esterified.

* * * * *